(12) United States Patent
Zhou et al.

(10) Patent No.: US 12,296,098 B2
(45) Date of Patent: May 13, 2025

(54) LINER FOR BREATHING MASK, BREATHING MASK, AND VENTILATION TREATMENT DEVICE

(71) Applicant: BMC Medical Co., LTD., Beijing (CN)

(72) Inventors: Mingzhao Zhou, Beijing (CN); Yajie Wang, Beijing (CN); Zhi Zhuang, Beijing (CN)

(73) Assignee: BMC MEDICAL CO., LTD., Beijing (CN)

( * ) Notice: Subject to any disclaimer, the term of this patent is extended or adjusted under 35 U.S.C. 154(b) by 922 days.

(21) Appl. No.: 17/419,603

(22) PCT Filed: Dec. 27, 2019

(86) PCT No.: PCT/CN2019/129344
§ 371 (c)(1),
(2) Date: Jun. 29, 2021

(87) PCT Pub. No.: WO2020/135762
PCT Pub. Date: Jul. 2, 2020

(65) Prior Publication Data
US 2022/0080145 A1 Mar. 17, 2022

(30) Foreign Application Priority Data
Dec. 29, 2018 (CN) .......................... 201811641531.3

(51) Int. Cl.
*A61M 16/06* (2006.01)

(52) U.S. Cl.
CPC .... *A61M 16/0622* (2014.02); *A61M 16/0611* (2014.02); *A61M 2210/0618* (2013.01); *A61M 2210/0625* (2013.01)

(58) Field of Classification Search
CPC .......... A61M 16/0611; A61M 16/0622; A61M 16/0616; A61M 16/0605; A62B 18/02; A62B 18/08; A61B 18/025
See application file for complete search history.

(56) References Cited

U.S. PATENT DOCUMENTS

| | | | | |
|---|---|---|---|---|
| 2,706,983 A | * | 4/1955 | Matheson | A62B 18/025 128/206.17 |
| 8,220,459 B2 | * | 7/2012 | Davidson | A62B 18/08 128/207.14 |

(Continued)

FOREIGN PATENT DOCUMENTS

| | | |
|---|---|---|
| CN | 1681553 | 10/2005 |
| CN | 101119763 | 2/2008 |

(Continued)

OTHER PUBLICATIONS

WIPO, International Search Report for PCT/CN2019/129344, Mar. 26, 2020.

(Continued)

*Primary Examiner* — Rachel T Sippel
*Assistant Examiner* — Gwynneth L Howell
(74) *Attorney, Agent, or Firm* — Hodgson Russ LLP

(57) ABSTRACT

A cushion includes an accommodating cavity for accommodating a nose or oronasal part, which is defined by a contact portion, a connecting portion and an intermediate portion. The contact portion is configured to be in sealing contact with a patient's face. The connecting portion is configured to connect with a frame of the respiratory mask. The intermediate portion is connected between the contact portion and the connecting portion. The intermediate portion is formed with a recess portion recessed toward the accommodating cavity. The recess portion is formed into an arc or ring shape extending in a circumferential direction of the cushion, which includes a first connecting wall and a second con- (Continued)

necting wall. A projection area S2 of the first connecting wall on a vertical plane is smaller than a projection area S1 of the second connecting wall.

9 Claims, 13 Drawing Sheets

(56)  References Cited

U.S. PATENT DOCUMENTS

| | | | |
|---|---|---|---|
| 2009/0000623 | A1 | 1/2009 | Lynch et al. |
| 2009/0095301 | A1* | 4/2009 | Hitchcock ......... A61M 16/0633 128/206.21 |
| 2009/0139526 | A1 | 6/2009 | Melidis et al. |
| 2011/0155139 | A1 | 6/2011 | Ho et al. |
| 2014/0261435 | A1* | 9/2014 | Rothermel ............ A61M 16/06 128/205.25 |
| 2014/0283842 | A1* | 9/2014 | Bearne .............. A61M 16/0666 128/206.24 |
| 2017/0246412 | A1 | 8/2017 | Melidis et al. |

FOREIGN PATENT DOCUMENTS

| | | |
|---|---|---|
| CN | 101822862 A | 9/2010 |
| CN | 104023777 | 9/2014 |
| CN | 204050596 | 12/2014 |
| CN | 204655726 | 9/2015 |
| CN | 207666956 | 7/2018 |
| CN | 109646779 | 4/2019 |
| CN | 209864958 | 12/2019 |
| EP | 3103499 | 12/2016 |
| JP | 2008526392 | 7/2008 |
| JP | 2008526393 | 7/2008 |

OTHER PUBLICATIONS

JPO, Notice of Reasons for Refusal for JP Application No. 2021-538478, Jul. 5, 2022.
EPO, Extended European Search Report for EP Application No. 19905841.3, Jan. 31, 2022.
CNIPA, First Office Action for CN Application No. 201811641531.3, Aug. 22, 2023.

* cited by examiner

LINER FOR BREATHING MASK, BREATHING MASK, AND VENTILATION TREATMENT DEVICE

CROSS-REFERENCE TO RELATED APPLICATIONS

The present application is a U.S. national phase entry under 35 U.S.C. § 371 of International Application PCT/CN2019/129344, filed on Dec. 27, 2019, which claims priority to Chinese Patent Application No. CN201811641531.3, filed on Dec. 29, 2018, the entire disclosures of which are incorporated herein by reference.

TECHNICAL FIELD

The present disclosure relates to the field of ventilation therapy apparatus; in particular, the present disclosure relates to a cushion for a respiratory mask, a respiratory mask with the cushion, and a ventilation therapy apparatus with the respiratory mask.

BACKGROUND

Non-invasive positive pressure ventilation has been widely used in the treatment of diseases such as obstructive sleep apnea (OSA), chronic obstructive pulmonary emphysema (COPD), etc. It is no longer required to insert a hose into patient's airway through a surgical operation; instead, a blower is used to deliver a continuous positive airway pressure (CPAP) or a variable positive airway pressure to the patient's airway through a pipeline and a patient interface device.

The patient interface device in non-invasive ventilation treatment usually includes a respiratory mask such as a nasal mask, an oronasal mask, a nasal pillow mask, and a full-face mask. A typical structure of the respiratory mask includes a frame, a cushion, an elbow, a connector, a headband, and so on. The cushion is fixed to the frame so that a gas chamber is formed by the cushion together with the frame, the elbow is connected to the frame through the connector to deliver a therapeutic gas into the gas chamber, and the headband is connected to the patient's head to fix the respiratory mask at a proper position of the patient's head. In use, the cushion is in contact with the patient's face to achieve sealing against the face, and the patient's mouth and/or nose are located in the gas chamber, with a support force between the cushion and the face generally varying with a tension of the headband.

For patients with OSA or COPD, it is usually necessary for them to wear the respiratory mask for a long time. Therefore, the structure of the cushion has a direct influence on sealing performance and comfort of wearing the respiratory mask. If the support force between the cushion and the face is too weak, it is difficult to form sealing therebetween. If the support force between the cushion and the face is too great, it will cause discomfort, especially at sensitive positions such as nose bridge, which may cause patient's refusal or resistance to treatment, and even cause allergies or red prints due to excessive pressing on the patient's face.

Therefore, it is necessary to provide a cushion for a respiratory mask with better sealing performance and comfort.

SUMMARY

In view of the above problems, an object of the present disclosure is to provide a cushion for a respiratory mask with better sealing performance and comfort, a respiratory mask with the cushion, and a ventilation therapy apparatus with the respiratory mask.

In order to achieve the above object, a first aspect of the present disclosure provides a cushion for a respiratory mask, the cushion comprises an accommodating cavity for accommodating a nose or oronasal part, as well as a contact portion, a connecting portion and an intermediate portion that are configured to define the accommodating cavity, the contact portion is configured to be in sealing contact with a patient's face, the connecting portion is configured to connect to a frame of the respiratory mask, and the intermediate portion is connected between the contact portion and the connecting portion, the intermediate portion is formed with a recess portion recessed toward the accommodating cavity, the recess portion is formed into an arc or ring shape extending in a circumferential direction of the cushion, the recess portion has a V-shaped cross section, and the recess portion comprises a first connecting wall and a second connecting wall connected to each other; and wherein the first connecting wall is disposed close to the contact portion, and a projection area $S_2$ of the first connecting wall on a vertical plane is smaller than a projection area $S_1$ of the second connecting wall on the vertical plane. It can be understood that a plane in which the patient's face lies when the patient is standing and looking at the front horizontally is approximately a vertical plane. With this design, under the same gas pressure (since a respiratory gas will be introduced into an accommodating cavity through an elbow and the cushion is sealed against the patient's face when the respiratory mask is in use, there will be a certain gas pressure in the accommodating cavity), a leftward thrust of the gas pressure to a second connecting wall is greater than a rightward thrust of the gas pressure to a first connecting wall, and the cushion exhibits an expanded state in a direction perpendicular to a plane a, which increases a support force between the patient's face and the contact portion, and improves the sealing effect and comfort.

Optionally, the recess portion is formed into a ring shape extending in the circumferential direction of the cushion, an end of the second connecting wall facing away from the first connecting wall is connected to the connecting portion, and the intermediate portion comprises a first portion which connects the contact portion with an end of the first connecting wall facing away from the second connecting wall. That is, in the cushion, the contact portion, the first portion, the first connecting wall, the second connecting wall, and the connecting portion are connected in this order in an axial direction of the cushion, and each of them is formed into a ring shape.

Optionally, a thickness of the connecting portion and a thickness of the first portion are larger than a thickness of the contact portion, so that the first portion with a larger thickness can reliably support the contact portion, and the connecting portion with a larger thickness can ensure a reliable connection with the frame; the thickness of the connecting portion and the thickness of the first portion are larger than a thickness of the first connecting wall and a thickness of the second connecting wall, which facilitates the first connecting wall and the second connecting wall to be deformed under the action of the gas pressure in the accommodating cavity, in other words, it facilitates extending or folding of the recess portion in the axial direction of the cushion around a hinge point b at the connection of the first connecting wall and the second connecting wall and a hinge point c at the connection of the second connecting wall and the connecting portion; and/or the thickness of the first connecting wall is set to gradually decrease from an end close to the first portion to an end close to the second connecting wall, and a thickness of an end of the first connecting wall that is close to the second connecting wall is equal to the thickness of the second connecting wall. It can be understood that the thickness of the second connecting wall is uniform, and the thickness of the first connecting wall transitions between the first portion and the second connecting wall.

Optionally, the cushion is divided in its circumferential direction into a nose bridge area, a cheek area and a philtrum or chin area, the recess portion is formed into an arc shape extending along the nose bridge area, an end of the second connecting wall facing away from the first connecting wall is connected to the connecting portion, and the intermediate portion comprises a first portion which connects the contact portion with an end of the first connecting wall facing away from the second connecting wall, and a second portion which connects the contact portion with the connecting portion.

Optionally, a thickness of the first portion is set to decrease from a top end of the nose bridge area to a bottom end of the nose bridge area, and a thickness of the first connecting wall and a thickness of the second connecting wall are set to increase from the top end of the nose bridge area to the bottom end of the nose bridge area;

at the top end of the nose bridge area, a thickness of the connecting portion and a thickness of the first portion are larger than a thickness of the second portion, so that the first portion with a larger thickness can reliably support the contact portion, and the connecting portion with a larger thickness can ensure a reliable connection with the frame; the thickness of the second portion is larger than a thickness of the first connecting wall and a thickness of the second connecting wall, the second connecting wall and the first connecting wall with relatively smaller thicknesses can ensure smooth extending or folding of the recess portion around the hinge point b and the hinge point c under the action of the gas pressure; and at the bottom end of the nose bridge area, the thickness of the first portion is the equal to the thickness of the first connecting wall, the thickness of the second connecting wall and the thickness of the second portion. The hinge point b and the hinge point c are gradually unified into one hinge point at the bottom end of the nose bridge area, resulting in a concentrated stress, with the above arrangement, the cushion can be prevented from rupturing, thereby effectively improving use durability of the cushion.

Optionally, the contact portion comprises a lip edge and a support edge connected to each other, the support edge is disposed close to the intermediate portion, and a thickness of the support edge is larger than a thickness of the lip edge, the thicker support edge can support the lip edge to a certain extent, and at the same time it can also ensure a stable connection with the intermediate portion, whereas the thinner lip edge can reduce the pressing of the respiratory mask on the patient's face; and/or a surface of the contact portion that is in contact with the patient's face is formed as an arc surface that conforms to a contour of the patient's face, in use, the contact portion is in contact with the patient's face, disperses a first contact force of the respiratory mask applied to the patient's face, and forms a seal between the patient's face and the respiratory mask.

Optionally, a thickness of the lip edge (121) is 0.2 mm-0.5 mm, preferably 0.3 mm-0.4 mm.

A second aspect of the present disclosure provides a respiratory mask, comprising a frame, as well as a cushion and an elbow that are connected to the frame, wherein the cushion is the above cushion for the respiratory mask.

Optionally, the frame comprises a cup, and the cushion is connected to the cup through the connecting portion.

A third aspect of the present disclosure provides a ventilation therapy apparatus, comprising a host for generating a therapeutic gas, and a respiratory mask in communication with a gas outlet of the host, wherein the respiratory mask is the above respiratory mask.

In the above technical solution, the cushion of the present disclosure is provided with a recess portion in an intermediate portion, which extends in a circumferential direction of the cushion and which is recessed toward the accommodating cavity, and a projection area $S_2$ of a first connecting wall of the recess portion on a plane in which the patient's face lie is smaller than a projection area $S_1$ of a second connecting wall of the recess portion on the plane in which the patient's face lies. When in use, the recess portion will apply an additional support force to the patient's face through the contact portion under the action of the gas pressure in the accommodating cavity, so that the cushion has a great sealing force in the case of a small tension of the headband, thereby bringing about better sealing performance and comfort.

Other features and advantages of the present disclosure will be described in detail in the following specific embodiments.

BRIEF DESCRIPTION OF THE DRAWINGS

Accompanying drawings are provided to enable a further understanding of the present disclosure. They constitute a part of the specification, and are used to interpret the present disclosure together with the following specific embodiments. However, the drawings do not constitute a limitation to the present disclosure. In the drawings.

REFERENCE SIGNS

10: cushion; 101: nose bridge area; 102: cheek area; 103: philtrum or chin area; 11: accommodating cavity; 12: contact portion; 121: lip edge; 122: support edge; 13: connecting portion; 131: first groove; 132: connecting hole; 14: intermediate portion; 140: recess portion; 141: first connecting wall; 142: second connecting wall; 143: first portion; 144: second portion; 145: second groove; 20: frame; 21: cup; 30: elbow.

DETAILED DESCRIPTION

Specific embodiments of the present disclosure will be described in detail below with reference to the accompanying drawings. It should be understood that the specific embodiments described herein are only used to illustrate and interpret the present disclosure, and are not used to limit the present disclosure.

Figure 1:
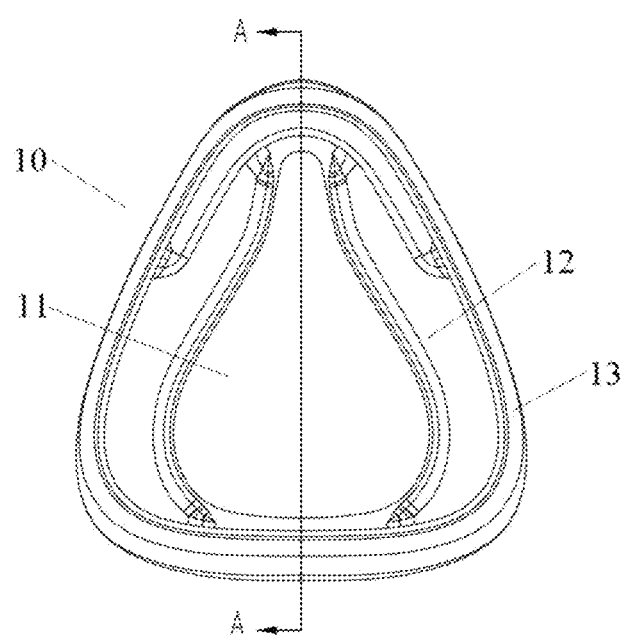
FIG. 1 is a rear view of an embodiment of a cushion of the present disclosure.

In the present disclosure, unless otherwise defined, terms for describing orientations such as "top" and "bottom" refer to the orientations shown in FIG. 1. Terms "inside" and "outside" refers to the inside and outside relative to the contour of each component itself.

A first aspect of the present disclosure provides a cushion for a respiratory mask. The cushion 10 includes an accommodating cavity 11 for accommodating the nose or oronasal part, as well as a contact portion 12, a connecting portion 13, and an intermediate portion 14 that are configured to define the accommodating cavity 11. The contact portion 12 is configured to be in sealing contact with patient's face, the connecting portion 13 is configured to connect with a frame 20 of the respiratory mask, and the intermediate portion 14 is connected between the contact portion 12 and the connecting portion 13. The intermediate portion 14 is formed with a recess portion 140 recessed toward the accommodating cavity 11. The recess portion 140 is formed into an arc or ring shape extending in a circumferential direction of the cushion 10. Preferably, the connecting portion 13 is disposed at an end of the intermediate portion 14, wherein the frame 20 may include a cup 21, and the cushion 10 is connected to the cup 21 through the connecting portion 13, that is, the intermediate portion 14 does not extend toward a cup 21 side, so that the cup 21 that is relatively rigid can be pressed against the patient's face, thus improving sealing performance of the cushion.

Figure 11:
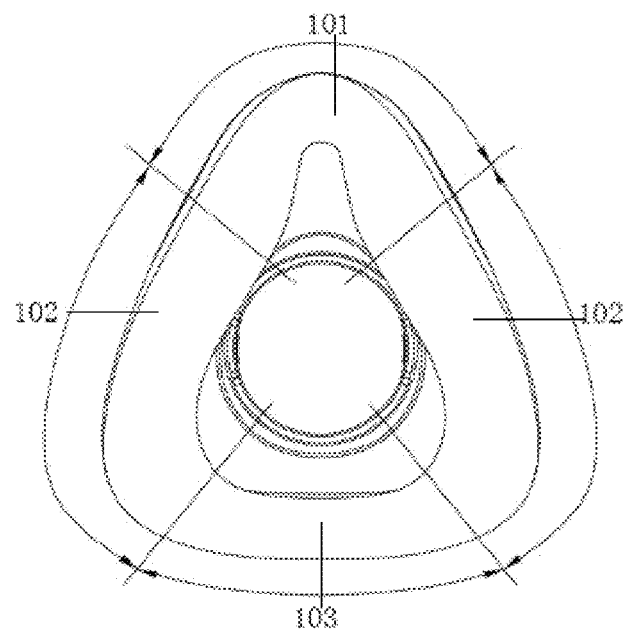
FIG. 11 is a schematic view of the cushion in FIG. 2 and the cup after they are installed, in which a nose bridge area, a cheek area and a philtrum or chin area are obtained by division.

According to a general shape of cushions in respiratory masks, it can be known that the contact portion 12, the connecting portion 13 and the intermediate portion 14 aforementioned are each formed into a ring shape (see FIGS. 1 and 2), and it can be understood that the ring shape may be either a closed ring structure or an open ring structure (that is, a part of the ring). In addition, it can be understood that if the respiratory mask is a nasal mask, the accommodating cavity 11 may be configured to accommodate the nose. In this case, the cushion 10 may be divided in its circumferential direction into a nose bridge area 101 (that is, an area at an upper part of the cushion that corresponds to the nose bridge, referring to FIG. 11), a cheek area 102 (that is, areas on both sides of the cushion that correspond to the cheeks, referring to FIG. 11) and a philtrum area 103 (that is, an area at a lower part of the cushion that corresponds to the philtrum, referring to FIG. 11). If the respiratory mask is an oronasal mask, the accommodating cavity 11 can be configured to accommodate both the mouth and the nose. In this case, the cushion 10 is divided in its circumferential direction into a nose bridge area 101, a cheek area 102 and a chin area 103 (that is, an area at the lower part of the cushion that corresponds to the chin, referring to FIG. 11). In the above, the recess portion 140 is formed into an arc or ring shape extending along the circumferential direction of the cushion 10, which means that the recess portion 140 may be formed on any segment of the circumferential contour of the cushion. For example, the recess portion 140 may be formed as an arc extending along any one or two of the nose bridge area 101, the cheek area 102 and the philtrum or chin area 103, and the recess portion 140 may also be formed as a ring extending along all the three areas of the nose bridge area 101, the cheek area 102 and the philtrum or chin area 103.

By adopting the above-mentioned technical solution, in which the intermediate portion 14 is provided with the recess portion 140 extending in the circumferential direction of the cushion 10 and recessed toward the accommodating cavity, during the use of the cushion 10 of the present disclosure, the recess portion 140 applies an additional support force to the patient's face through the contact portion 12 under the action of a gas pressure in the accommodating cavity, so that a great sealing force is obtained for the cushion 10 in the case of a weak tension of the headband, thus bringing about better sealing performance and comfort of the cushion. In other words, when a certain sealing force is required for the cushion, the sealing force completely comes from a tension of the headband in the case of the cushion in the prior art (in which no recess portion is provided in the intermediate portion). Accordingly, in order to increase the sealing performance of the cushion, it is necessary to increase the tension of the headband, which will affect the wearing comfort. In the present disclosure, by using the above technical solution, the sealing force required for the cushion can be provided by the tension of the headband and the support force of the recess portion 140 altogether, so that only a small tension of the headband is required, thus improving the wearing comfort.

Figure 3:
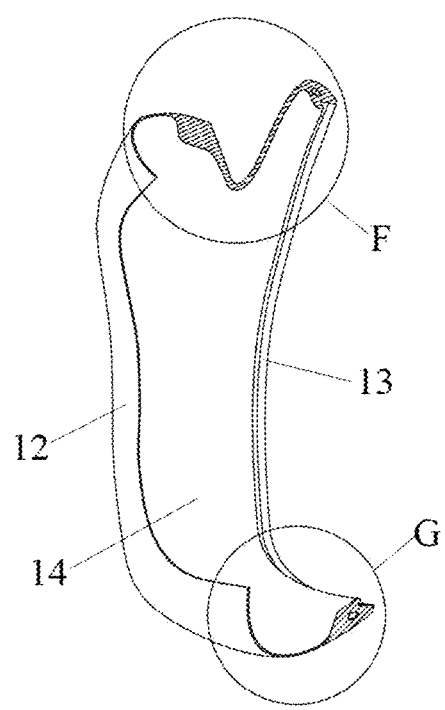
FIG. 3 is a cross-sectional view taken along line A-A in FIG. 1.
Figure 4:
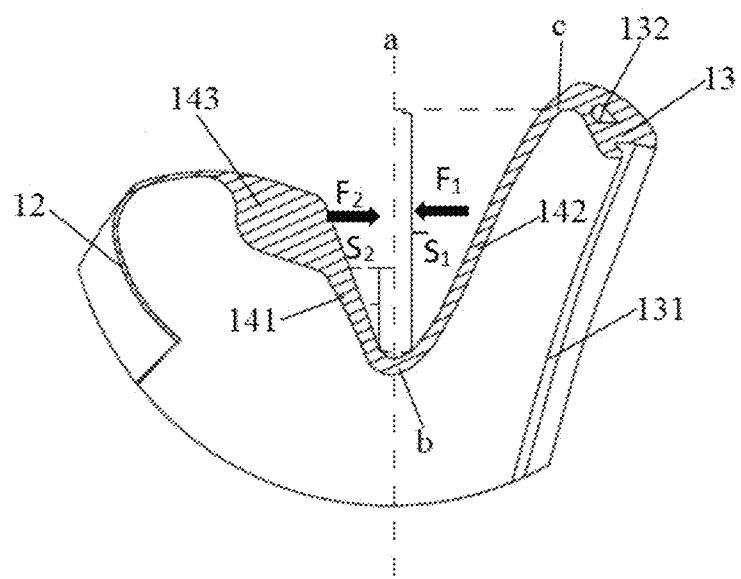
FIG. 4 is an enlarged view of part F in FIG. 3.
Figure 15:
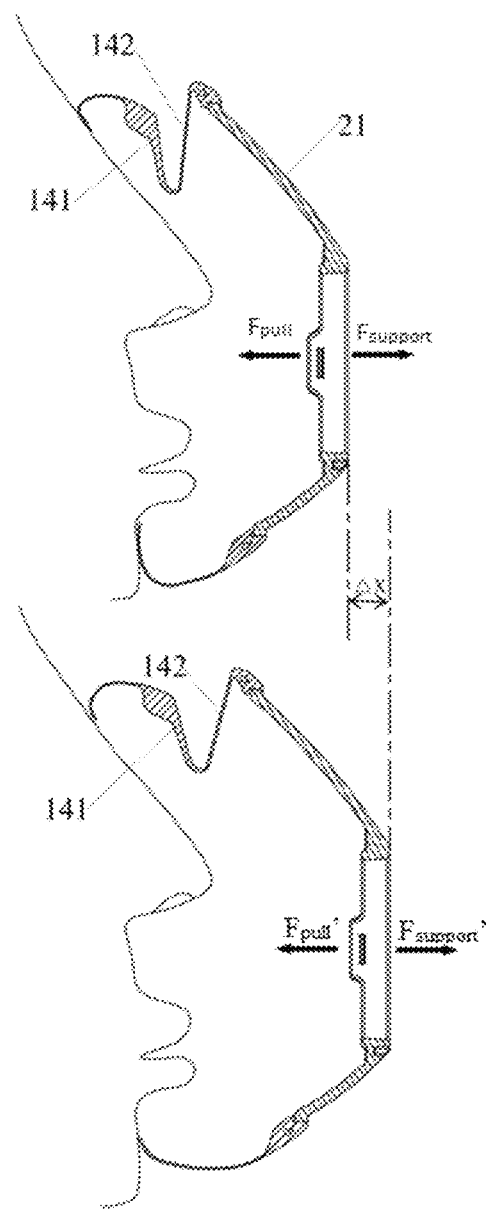
FIG. 15 is a schematic view showing a comparison of the cushion before and after ventilation expansion.

In the present disclosure, the recess portion 140 may have any appropriate shape, as long as it can provide an additional support force to the contact portion 12 under the gas pressure. Specifically, according to an embodiment of the present disclosure, as shown in FIGS. 3 and 4, the cross section of the recess portion 140 is substantially V-shaped, and the recess portion 140 includes a first connecting wall 141 and a second connecting wall 142 connected to each other. The first connecting wall 141 is disposed close to the contact portion 12, and a projection area $S_2$ of the first connecting wall 141 on the plane in which the patient's face lies is smaller than a projection area $S_1$ of the second connecting wall 142 on the plane. It can be understood that the first connecting wall 141 and the second connecting wall 142 form two side walls of the V shape, but the first connecting wall 141 and the second connecting wall 142 do not need to be straight, but may have a certain curvature (for example, as shown in FIG. 4). The first connecting wall 141 and the second connecting wall 142 may be directly connected, or may be connected via an arc surface and/or plane, and/or connected via a corrugated surface, and the first connecting wall 141 and the second connecting wall 142 do not need to be equal in length. In addition, it should be noted that since the material of the cushion 10 is usually made of a soft material, it may be deformed to some extent after the wearing. Therefore, in actual production, it is necessary to ensure that the projection area $S_2$ of the first connecting wall 141 of the cushion 10 on the plane in which the patient's face lies is smaller than the projection area $S_1$ of the second connecting wall 142 on the plane when the respiratory mask is in a stable state after being worn by the patient. It can be understood that the plane in which the patient's face lies when the patient is standing and looking at the front horizontally is approximately a vertical plane. Referring to FIG. 4, the plane in which the patient's face lies when the patient is standing and looking at the front horizontally may be approximately the vertical plane, that is, plane a. The projection area $S_2$ of the first connecting wall 141 on the plane a is smaller than the projection area $S_1$ of the second connecting wall 142 on the plane a. With this design, under the same gas pressure (since a respiratory gas will be introduced into the accommodating cavity 11 through an elbow 30 and the cushion is sealed against the patient's face when the respiratory mask is in use, there will be a certain gas pressure in the accommodating cavity 11), a leftward thrust $F_1$ of the gas pressure applied to the second connecting wall 142 is greater than a rightward thrust $F_2$ of the gas pressure applied to the first connecting wall 141, and the cushion 10 exhibits an expanded state in a direction perpendicular to the plane a; for example, the cushion 10 shown in FIG. 15 expands by $\Delta X$ with respect to an original state, thereby increasing the support force between the patient's face and the contact portion 12, and improving the sealing effect and comfort. The specific principle is described as follows.

In the original state during ventilation (see the upper one of FIG. 15), if the pressure from the gas is defined as P, a contact area between the cushion 10 and the patient's face is defined as S, a tightening force of the headband is defined as $F_{pull}$, and the support force of the patient's face to the cushion 10 is defined as $F_{support}$, then the following formula is satisfied:

$$F_{pull} = F_{support} + PS \qquad (1)$$

The recess portion 140 is provided on the cushion 10, and it serves to provide an expansion length $\Delta X$ in the direction perpendicular to the plane a when in a ventilating state. An elastic stiffness coefficient of the headband is defined as K, an increase amount of the tightening force of the headband is $K\Delta X$, the support force of the patient's face to the cushion in the expanded state (see the lower one of FIG. 15) is defined as $F_{support}'$, and then the following formula is satisfied:

$$F_{pull}' = F_{pull} + K\Delta X = F_{support}' + PS \qquad (2)$$

Through a comprehensive comparison of the two formulas ① and ②, it can be seen that $F_{support}' > F_{support}$, that is, under the same conditions, the structure of the recess portion 140 increases the support force between the patient's face and the cushion and improves the sealing effect. On the other hand, the expansion length $\Delta X$ makes the cushion form an expanded balloon structure, which is much softer, thereby improving the wearing comfort.

In actual use, since a height of the nose bridge varies from person to person, for patients with a higher nose bridge, the recess portion 140 may come into contact with the nose bridge, thereby affecting wearing experience of the respiratory mask. Therefore, in order to prevent the recess portion 140 from touching the nose bridge of the patient when in use, the recess portion 140 may be configured to be inclined toward the side facing away from the patient's face. That is, a bisecting plane of the recess portion 140 (an included angle between the bisecting plane and the first connecting wall 141 is equal to an included angle between the bisecting plane and the second connecting wall 142) is inclined toward the side facing away from the patient's face with respect to the plane a in which the patient's face lies, which can increase a distance between the recess portion 140 and the patient's nose bridge.

An included angle between the bisecting plane of the recess portion 140 and the plane a in which the patient's face lies is preferably 0-45°, more preferably 0-30°. In addition, since the recess portion 140 is usually squeezed to deform during the actual wearing, the strength of the first connecting wall 141 can be made greater than that of the second connecting wall 142 in order to further prevent the recess portion 140 from coming into contact with the nose bridge of the patient. In this way, the first connecting wall 141 has a greater resistance to deformation than the second connecting wall 142, so that the recess portion 140 is deformed in a direction away from the nose bridge when the cushion is squeezed after the wearing.

In order to make the strength of the first connecting wall 141 greater than that of the second connecting wall 142, according to an embodiment of the present disclosure, a thickness of the first connecting wall 141 may be set larger than a thickness of the second connecting wall 142. According to another embodiment of the present disclosure, the first connecting wall 141 may be made of a material harder than that of the second connecting wall 142. For example, the first connecting wall 141 may be made of silicone with a density larger than the material of the second connecting wall 142.

In addition, when the recess portion 140 is formed into an arc shape, in order to release internal stress and increase deformability of the recess portion 140 (that is, to facilitate expanding and folding of the recess portion 140), an inner surface of the intermediate portion 14 may be formed with two second grooves 145 (see FIG. 14) respectively disposed around two ends of the recess portion 140, that is, regions of the intermediate portion 14 respectively around the two ends are configured as thinned regions. The second groove 145 may be formed into any shape, and a thickness of a bottom wall of the second grooves 145 (that is, a thickness of the thinned regions) is preferably 0.5 mm-1.5 mm, more preferably 0.8 mm-1.2 mm.

Specifically, according to an embodiment of the present disclosure, regarding the extension length of the recess portion 140 in the circumferential direction of the cushion 10, the recess portion 140 is formed into a ring shape extending in the circumferential direction of the cushion 10. An end of the second connecting wall 142 facing away from the first connecting wall 141 is connected to the connecting portion 13. The intermediate portion 14 includes a first portion 143 which connects the contact portion 12 with an end of the first connecting wall 141 facing away from the second connecting wall 142. That is, in the cushion 10, the contact portion 12, the first portion 143, the first connecting wall 141, the second connecting wall 142, and the connecting portion 13 are connected in this order in an axial direction of the cushion 10, and each of them is formed into a ring shape.

Preferably, a thickness of the connecting portion 13 and a thickness of the first portion 143 are each larger than a thickness of the contact portion 12, so that the first portion 143 with a larger thickness can reliably support the contact portion 12, and the connecting portion 13 with a larger thickness can ensure a reliable connection with the frame 20. The present disclosure does not impose limitations on a relationship between magnitudes of the thickness of the connecting portion 13 and the thickness of the first portion 143. In addition, the thickness of the connecting portion 13 and the thickness of the first portion 143 are made larger than the thickness of the first connecting wall 141 and the thickness of the second connecting wall 142, which facilitates the first connecting wall 141 and the second connecting wall 142 to be deformed under the action of the gas pressure in the accommodating cavity 11. In other words, it facilitates extending or folding of the recess portion 140 in the axial direction of the cushion 10 (that is, the direction perpendicular to the plane a in FIG. 4) around a hinge point b at the connection of the first connecting wall 141 and the second connecting wall 142 and a hinge point c at the connection of the second connecting wall 142 and the connecting portion 143 (see FIG. 4).

Preferably, the thickness of the first connecting wall 141 is set to gradually decrease from an end close to the first portion 143 to an end close to the second connecting wall 142, and a thickness of the end of the first connecting wall 141 that is close to the second connecting wall 142 is equal to the thickness of the second connecting wall 142. It can be understood that the thickness of the second connecting wall 142 is uniform, and the thickness of the first connecting wall 141 transitions between the first portion 142 and the second connecting wall 142.

Figure 13:
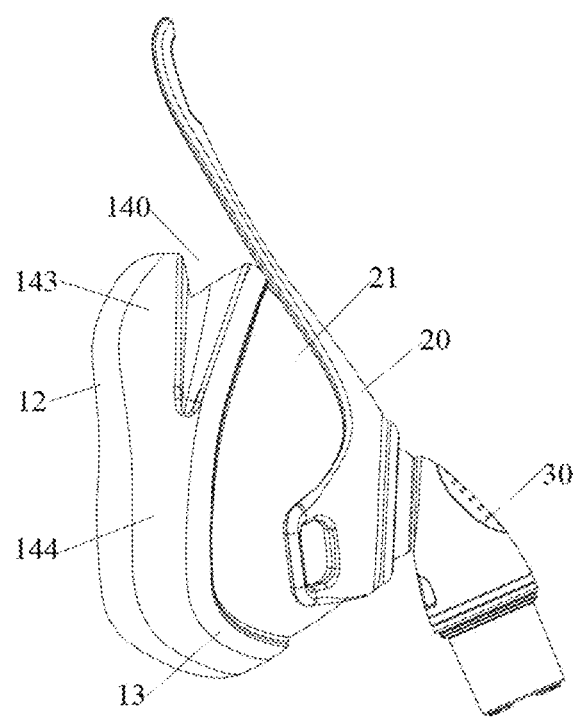
FIG. 13 is a right-side view of FIG. 12.

According to another embodiment of the present disclosure, as shown in FIGS. 3 and 13, the recess portion 140 is formed into an arc shape extending along the nose bridge area 101, and an end of the second connecting wall 142 facing away from the first connecting wall 141 is connected to the connecting portion 13. The intermediate portion 14 includes a first portion 143 connecting the contact portion 12 with an end of the first connecting wall 141 facing away from the second connecting wall 142, and a second portion 144 connecting the contact portion 12 with the connecting portion 13.

Figure 6:
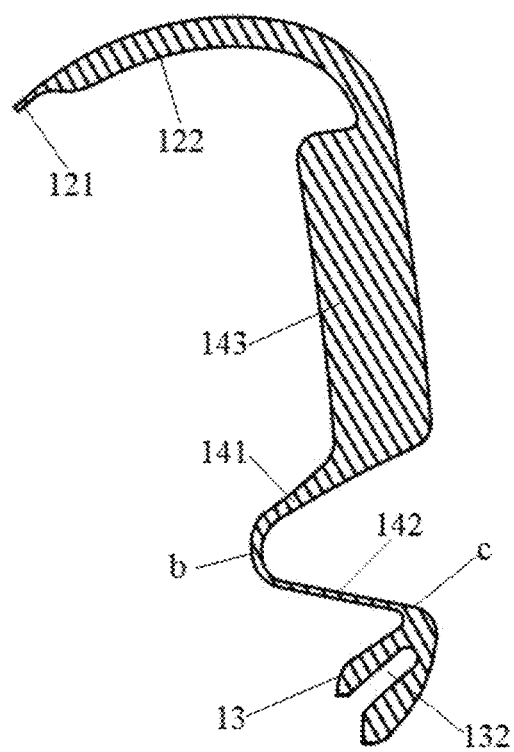
FIG. 6 is a cross-sectional view taken along line B-B in FIG. 2.
Figure 7:
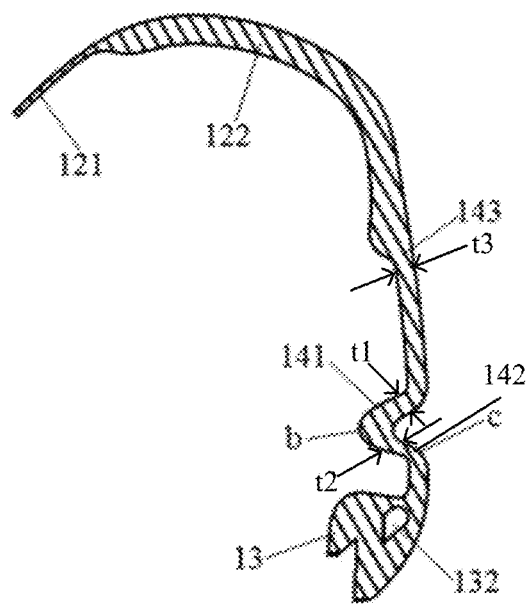
FIG. 7 is a cross-sectional view taken along line C-C in FIG. 2.

Preferably, the thickness of the first portion 143 is set to decrease from a top end of the nose bridge area 101 to a bottom end of the nose bridge area 101 (see FIGS. 4, 6 and 7), and the thickness of the first connecting wall 141 and the thickness of the second connecting wall 142 are set to increase from the top end of the nose bridge area 101 to the bottom end of the nose bridge area 101 (see FIGS. 4, 6 and 7). At the top end of the nose bridge area 101, the thickness of the connecting portion 13 and the thickness of the first portion 143 are larger than the thickness of the second portion 144 (so that the first portion 143 with a larger thickness can reliably support the contact portion 12, and the connecting portion 13 with a larger thickness can ensure a reliable connection with the frame 20). The thickness of the second portion 144 is larger than the thickness of the first connecting wall 141 and the thickness of the second connecting wall 142 (the second connecting wall 142 and the first connecting wall 141 with relatively smaller thicknesses can ensure smooth extending or folding of the recess portion 140 around the hinge point b and the hinge point c under the action of the gas pressure). At the bottom end of the nose bridge area 101, the thickness t3 of the first portion 143 is substantially equal to the thickness t1 of the first connecting wall 141, the thickness t2 of the second connecting wall 142 and the thickness of the second portion 144. The hinge point b and the hinge point c are gradually unified into one hinge point (see FIG. 7) at the bottom end of the nose bridge area 101, resulting in a concentrated stress. With the above arrangement, the cushion can be prevented from rupturing, thereby effectively improving use durability of the cushion.

In the above, the thickness of the first portion 143 at the top end of the nose bridge area 101 may be 1 mm-8 mm, preferably 3 mm-6 mm.

Figure 5:
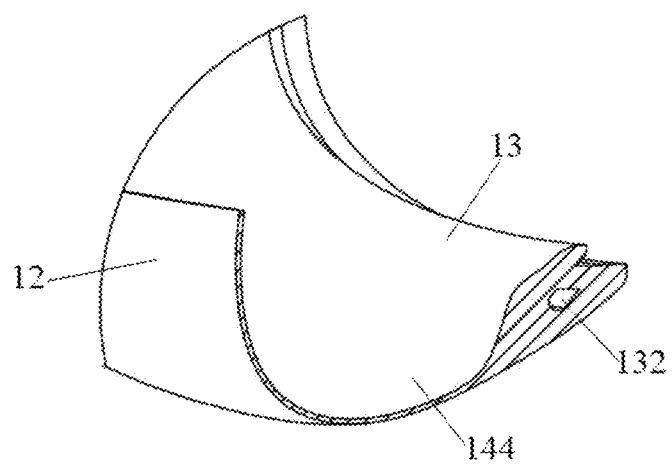
FIG. 5 is an enlarged view of part G in FIG. 3.
Figure 8:
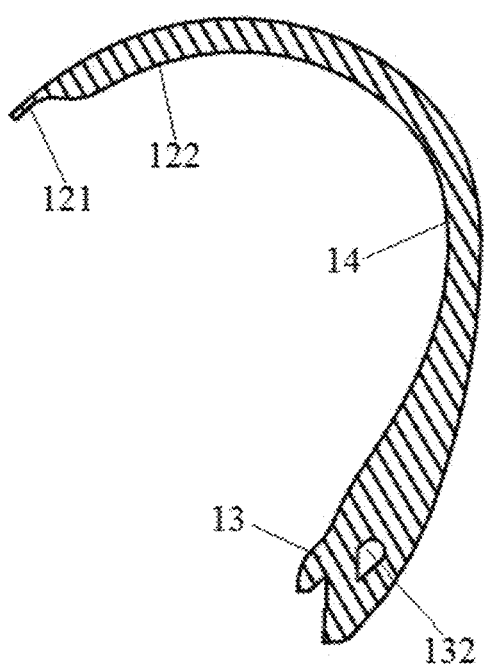
FIG. 8 is a cross-sectional view taken along line D-D in FIG. 2.

In the present disclosure, a surface of the contact portion 12 that is in contact with the patient's face may be formed as an arc surface that conforms to a contour of the patient's face. In use, the contact portion 12 is in contact with the patient's face, disperses a first contact force of the respiratory mask applied to the patient's face, and forms a seal between the patient's face and the respiratory mask. The contact portion 12 may include a lip edge 121 and a support edge 122 connected to each other. The support edge 122 is disposed close to the intermediate portion 14, and a thickness of the support edge 122 is larger than a thickness of the lip edge 121 (see FIGS. 6-8). It can be understood that the lip edge 121 and the support edge 122 are both formed into a ring shape. The thicker support edge 122 can support the lip edge 121 to a certain extent, and at the same time it can also ensure a stable connection with the intermediate portion 14; whereas the thinner lip edge 121 can reduce the pressing of the respiratory mask on the patient's face. The lip edge 121 is the softest and thinnest part of the cushion 10, and the thickness of the lip edge 121 may be 0.2 mm-0.5 mm, preferably 0.3 mm-0.4 mm. In addition, since the nose bridge and the chin are more sensitive, areas of the support edge 122 that correspond to the nose bridge and the chin may be set to have an equal thickness to the lip edge 121 (see FIGS. 4 and 5) in order to further improve comfort of the respiratory mask and reduce the pressing on the nose bridge and the chin.

Figure 2:
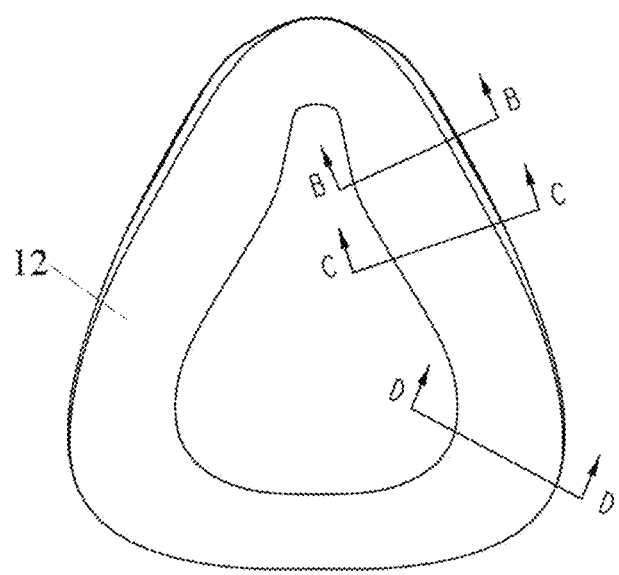
FIG. 2 is a front view of FIG. 1.

In addition, as shown in FIGS. 1 and 2, the accommodating cavity 11 may be set narrower at an upper part close to the nose bridge, and wider at a lower part close to the chin. With this design, the upper part can be matched with the patient's nose bridge during wearing, which can limit positional freedom of the cushion to a certain extent and reduce the pressing of the cushion on the nose bridge.

In the present disclosure, the cushion 10 may be made of a relatively soft and easily deformable material, such as silicone, and it may also be made of a known relatively soft and biocompatible material. The cushion 10 is preferably integrally formed, and it can be molded by any suitable process, such as injection molding, blow molding, and the like.

A second aspect of the present disclosure provides a respiratory mask, which includes a frame 20, as well as a cushion and an elbow 30, both of which are connected to the frame 20, and the cushion is the above-mentioned cushion 10 of the respiratory mask.

Figure 9:
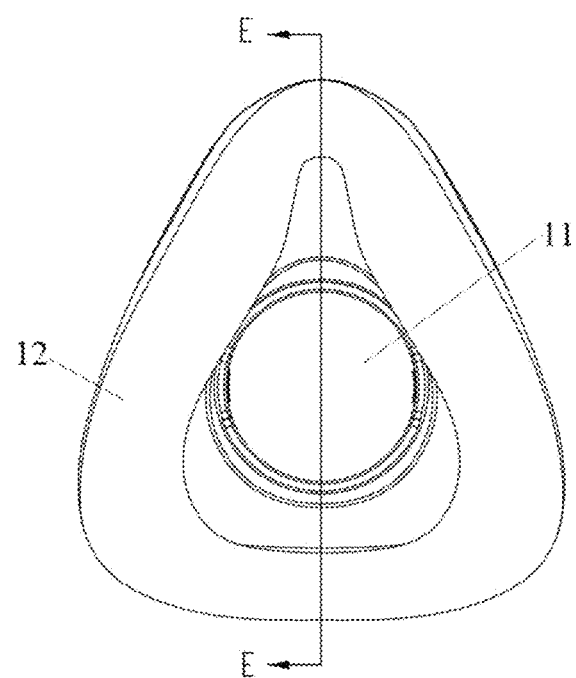
FIG. 9 is a schematic view of the cushion in FIG. 2 and a cup after they are installed.
Figure 10:
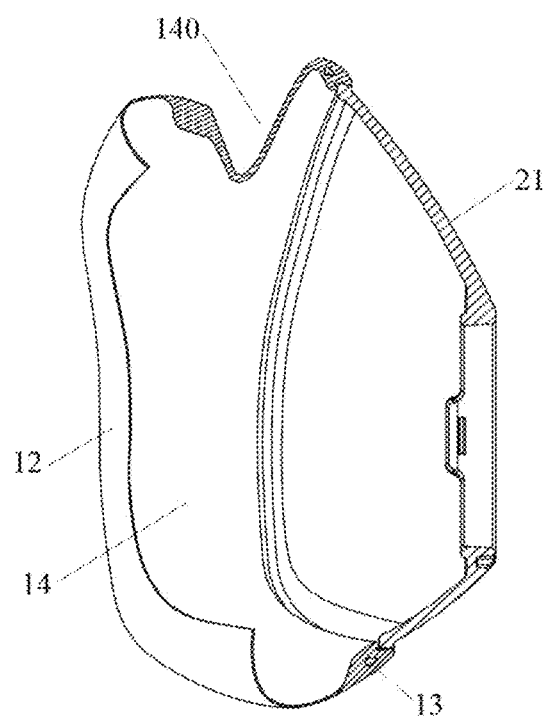
FIG. 10 is a cross-sectional view taken along line E-E in FIG. 9.
Figure 12:
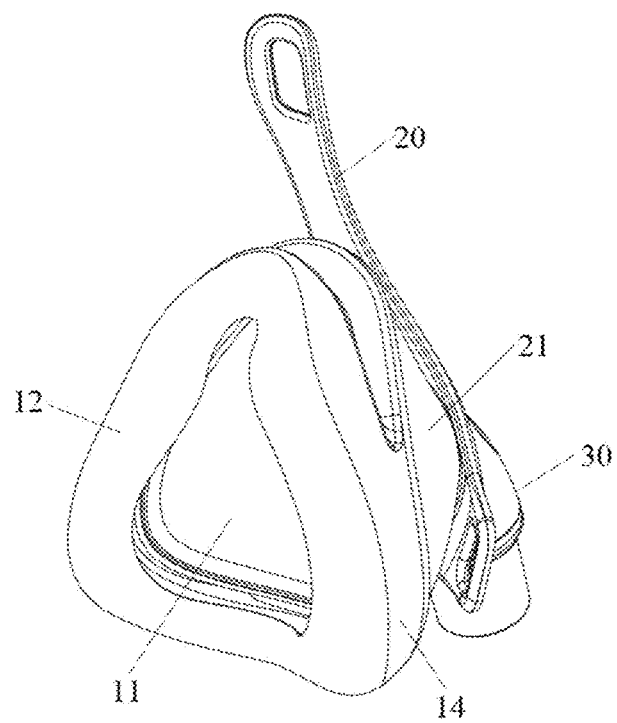
FIG. 12 is a perspective view of an embodiment of a respiratory mask of the present disclosure.

As shown in FIGS. 12 and 13, the frame 20 may include a cup 21, and the cushion 10 is connected to the cup 21 through the connecting portion 13. Specifically, as shown in FIGS. 9 and 10, a first groove 131 is provided on a side of the connecting portion 13 facing away from the intermediate portion 14, and the cushion 10 may be snap-fitted to a flange on the cup 21 through the first groove 131 (see FIG. 13). In addition, in order to further enhance firmness of the connection between the cushion 10 and the cup 21, the cushion 10 may be injection-molded onto the cup 21 during production. The cup 21 may be provided with a connecting rib which, after completion of the injection, will wrap into a connecting hole 132 of the connecting portion 13, so that the cup 21 is firmly connected with the cushion. Of course, the cushion 10 may also be connected to the cup 21 by any other known method.

Figure 14:
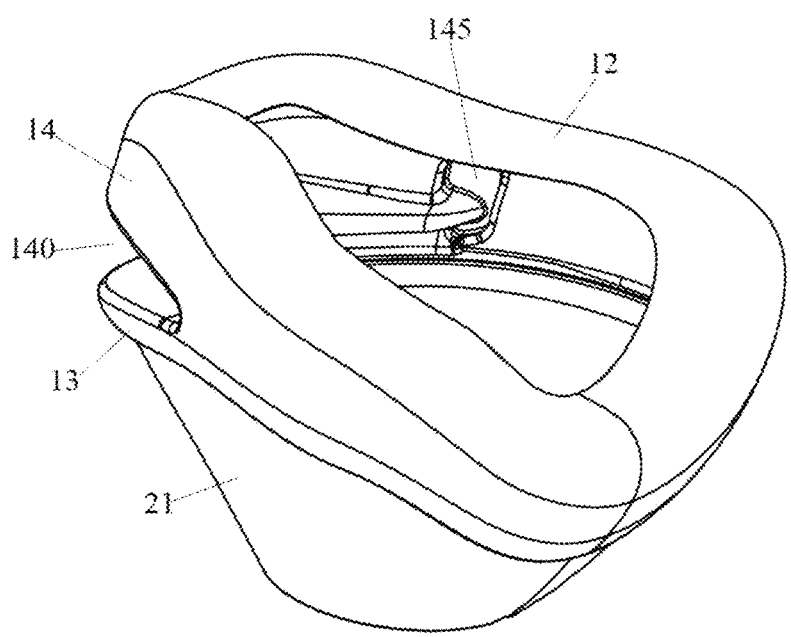
FIG. 14 is a perspective view of another embodiment of the cushion and the cup of the present disclosure.

Preferably, the connecting portion 13 is disposed at an end of the second connecting wall 142, and the second connecting wall 142 forms a cone structure with the connecting portion 13 and the cup 21 (see FIG. 14).

A third aspect of the present disclosure provides a ventilation therapy apparatus, which includes a machine for generating a therapeutic gas and a respiratory mask in communication with a gas outlet of the machine, and the respiratory mask is the above-mentioned respiratory mask.

The ventilation therapy apparatus may be a respirator.

The preferred embodiments of the present invention are described in detail above with reference to the accompanying drawings. However, the present invention is not limited to the specific details in the above-mentioned embodiments. Within the scope of the technical concept of the present invention, many simple modifications can be made to the technical solutions of the present invention. These simple modifications all belong to the protection scope of the present invention.

In addition, it should be noted that the various specific technical features described in the foregoing specific embodiments can be combined in any suitable manner, provided that there is no contradiction. In order to avoid unnecessary repetition, various possible combinations are not described separately in the present invention.

In addition, various different embodiments of the present invention can also be combined arbitrarily, as long as they do not violate the idea of the present invention, they should also be regarded as the disclosed content of the present invention.

The invention claimed is:

1. A cushion for a respiratory mask, wherein the cushion (10) comprises an accommodating cavity (11) for accommodating a nose or oronasal part, as well as a contact portion (12), a connecting portion (13) and an intermediate portion (14) that are configured to define the accommodating cavity (11); the contact portion (12) is configured to be in sealing contact with a patient's face, the connecting portion (13) is configured to connect to a frame (20) of the respiratory mask, and the intermediate portion (14) is connected between the contact portion (12) and the connecting portion (13); the intermediate portion (14) is formed with a recess portion (140) recessed toward the accommodating cavity (11), the recess portion (140) is formed into an arc shape extending in a circumferential direction of the cushion (10), and the recess portion (140) comprises a first connecting wall (141) and a second connecting wall (142) connected to each other; and wherein the first connecting wall (141) is disposed close to the contact portion (12), and a projection area $S_2$ of the first connecting wall (141) on a vertical plane is smaller than a projection area $S_1$ of the second connecting wall (142) on the vertical plane;

the cushion (10) is divided in its circumferential direction into a nose bridge area (101), a cheek area (102) and a philtrum or chin area (103), the recess portion (140) is formed into the arc shape extending along the nose bridge area (101), an end of the second connecting wall (142) facing away from the first connecting wall (141) is connected to the connecting portion (13), and the intermediate portion (14) comprises a first portion (143) which connects the contact portion (12) with an end of the first connecting wall (141) facing away from the second connecting wall (142), and a second portion (144) which connects the contact portion (12) with the connecting portion (13);

a thickness of the first portion (143) is set to decrease from a top end of the nose bridge area (101) to a bottom end of the nose bridge area (101), and a thickness of the first connecting wall (141) and a thickness of the second connecting wall (142) are set to increase from the top end of the nose bridge area (101) to the bottom end of the nose bridge area (101);

at the top end of the nose bridge area (101), a thickness of the connecting portion (13) and a thickness of the first portion (143) are larger than a thickness of the second portion (144), and the thickness of the second portion (144) is larger than a thickness of the first connecting wall (141) and a thickness of the second connecting wall (142); and at the bottom end of the nose bridge area (101), the thickness of the first portion (143) is equal to the thickness of the first connecting wall (141), the thickness of the second connecting wall (142) and the thickness of the second portion (144).

2. The cushion for the respiratory mask according to claim 1, wherein:

the contact portion (12) comprises a lip edge (121) and a support edge (122) connected to each other, the support edge (122) is disposed close to the intermediate portion (14), and a thickness of the support edge (122) is larger than a thickness of the lip edge (121); and/or a surface of the contact portion (12) that is in contact with the patient's face is formed as an arc surface that conforms to a contour of the patient's face.

3. The cushion for the respiratory mask according to claim 2, wherein a thickness of the lip edge (121) is 0.2 mm-0.5 mm.

4. The cushion for the respiratory mask according to claim 3, wherein the thickness of the lip edge (121) is 0.3 mm-0.4 mm.

5. A respiratory mask, comprising a frame (20), as well as a cushion and an elbow (30) that are connected to the frame (20), wherein the cushion comprises an accommodating cavity (11) for accommodating a nose or oronasal part, as well as a contact portion (12), a connecting portion (13) and an intermediate portion (14) that are configured to define the accommodating cavity (11); the contact portion (12) is configured to be in sealing contact with a patient's face, the connecting portion (13) is configured to connect to a frame (20) of the respiratory mask, and the intermediate portion (14) is connected between the contact portion (12) and the connecting portion (13); the intermediate portion (14) is formed with a recess portion (140) recessed toward the accommodating cavity (11), the recess portion (140) is formed into an arc shape extending in a circumferential direction of the cushion (10), and the recess portion (140) comprises a first connecting wall (141) and a second connecting wall (142) connected to each other; and wherein the first connecting wall (141) is disposed close to the contact portion (12), and a projection area $S_2$ of the first connecting wall (141) on a vertical plane is smaller than a projection area $S_1$ of the second connecting wall (142) on the vertical plane;

the cushion (10) is divided in its circumferential direction into a nose bridge area (101), a cheek area (102) and a philtrum or chin area (103), the recess portion (140) is formed into the arc shape extending along the nose bridge area (101), an end of the second connecting wall (142) facing away from the first connecting wall (141) is connected to the connecting portion (13), and the intermediate portion (14) comprises a first portion (143) which connects the contact portion (12) with an end of the first connecting wall (141) facing away from the second connecting wall (142), and a second portion (144) which connects the contact portion (12) with the connecting portion (13);

a thickness of the first portion (143) is set to decrease from a top end of the nose bridge area (101) to a bottom end of the nose bridge area (101), and a thickness of the first connecting wall (141) and a thickness of the second connecting wall (142) are set to increase from the top end of the nose bridge area (101) to the bottom end of the nose bridge area (101);

at the top end of the nose bridge area (101), a thickness of the connecting portion (13) and a thickness of the first portion (143) are larger than a thickness of the second portion (144), and the thickness of the second portion (144) is larger than a thickness of the first connecting wall (141) and a thickness of the second connecting wall (142); and at the bottom end of the nose bridge area (101), the thickness of the first portion (143) is equal to the thickness of the first connecting wall (141), the thickness of the second connecting wall (142) and the thickness of the second portion (144).

6. The respiratory mask according to claim 5, wherein the frame (20) comprises a cup (21), and the cushion (10) is connected to the cup (21) through the connecting portion (13); and/or the recess portion (140) has a V-shaped cross section.

7. A ventilation therapy apparatus, comprising a host for generating a therapeutic gas, wherein the respiratory mask is the respiratory mask according to claim 5, and the respiratory mask in communication with a gas outlet of the host.

8. The respiratory mask according to claim 5, wherein:
the contact portion (12) comprises a lip edge (121) and a support edge (122) connected to each other, the support edge (122) is disposed close to the intermediate portion (14), and a thickness of the support edge (122) is larger than a thickness of the lip edge (121); and/or a surface of the contact portion (12) that is in contact with the patient's face is formed as an arc surface that conforms to a contour of the patient's face.

9. The respiratory mask according to claim 5, wherein a thickness of a lip edge (121) is 0.2 mm-0.5 mm.

* * * * *